United States Patent [19]

Keller et al.

[11] 4,254,100

[45] Mar. 3, 1981

[54] VITAMIN A COMPOSITIONS

[75] Inventors: Hans E. Keller; Heinrich Klaeui, both of Riehen, Switzerland

[73] Assignee: Hoffmann-La Roche Inc., Nutley, N.J.

[21] Appl. No.: 128,078

[22] Filed: Mar. 7, 1980

Related U.S. Application Data

[63] Continuation of Ser. No. 885,984, Mar. 13, 1978, abandoned.

[30] Foreign Application Priority Data

Mar. 25, 1977 [CH] Switzerland .................. 3811/77

[51] Int. Cl.³ .................. A61K 9/40; A61K 9/32; A61K 9/34; A61K 31/07
[52] U.S. Cl. .................. 424/37; 424/31; 424/32; 424/34; 424/35; 424/344
[58] Field of Search .................. 424/31, 32, 34, 35, 424/37, 344

[56] References Cited

U.S. PATENT DOCUMENTS

| | | | |
|---|---|---|---|
| 2,183,053 | 12/1939 | Taylor | 424/37 |
| 2,218,591 | 10/1940 | Taylor | 424/22 |
| 2,218,592 | 10/1940 | Taylor | 424/22 |
| 2,375,279 | 5/1945 | Buxton et al. | 424/37 |
| 2,643,209 | 6/1953 | Goett et al. | 424/37 |
| 2,824,807 | 2/1958 | Lastor et al. | 424/37 |
| 2,987,444 | 6/1961 | Allardyce | 424/37 XV |
| 3,056,728 | 10/1962 | Ohtaki | 424/37 XV |
| 3,202,731 | 8/1965 | Grevenstuk et al. | 424/37 XV |
| 3,445,563 | 5/1969 | Clegg et al. | 424/37 XV |
| 3,565,559 | 2/1971 | Sato et al. | 424/37 |

*Primary Examiner*—Shep K. Rose
*Attorney, Agent, or Firm*—Jon S. Saxe; Bernard S. Leon; George M. Gould

[57] ABSTRACT

Microcrystalline vitamin A acetate dry free-flowing powders containing microcrystalline vitamin A acetate and a process for their preparation are disclosed.

11 Claims, No Drawings

4,254,100

VITAMIN A COMPOSITIONS

This is a continuation, of application Ser. No. 885,984 filed Mar. 13, 1978, now abandoned.

BACKGROUND OF THE INVENTION

Compositions containing vitamin A acetate or other vitamin A compounds are well-known in the prior art. However, in these compositions the vitamin A component is in neither crystalline nor microcrystalline form but rather in its oil form or in an oil-dissolved form. These preparations usually contain a protective colloid, such as gelatin. However, the stability of such products is limited since, at the required high vitamin A concentration, the oily vitamins readily pass through the protective colloid.

In other attempts to increase the stability of non-crystalline vitamin A compositions, antioxidants were added thereto. The presence of these antioxidants further reduced the applicability of these vitamin A compositions.

A process for the manufacture of dry preparations of vitamin A acetate in crystalline form is described in U.S. Pat. No. 2,643,209. The process involves the emulsification of crystalline vitamin A acetate in an aqueous gelatin solution. The emulsion is subsequently suspended in small droplets in mineral or vegetable oil and then cooled. In the resulting compositions, however, the vitamin A acetate is not in crystalline form.

SUMMARY OF THE INVENTION

This invention is directed to the preparation of microcrystalline vitamin A acetate and dry, free-flowing compositions wherein the vitamin A acetate is present in microcrystalline form.

By the process of this invention, microcrystalline vitamin A acetate is prepared by homogenization of molten vitamin A acetate in a suitable medium with subsequent rapid cooling of the mixture while continuing the particular homogenization technique. Dry powders can be prepared from the resulting microcrystals.

DETAILED DESCRIPTION OF THE INVENTION

Microcystalline vitamin A acetate or dry, free-flowing compositions containing microcrystalline vitamin A acetate can be prepared by:

(a) homogenizing molten or wet-milled vitamin A acetate in water or in an aqueous solution containing from about 0.1% to about 5% by weight, based on the weight of the solution, of an edible, water-soluble carrier composition and (b) cooling the resulting emulsion to about 15° C. while continuing the homogenization technique. If desired, the resulting vitamin A acetate microcrystals can be converted to beadlets.

The edible, water-soluble carrier composition can be either water-soluble protective colloid or an emulsifier.

Examples of acceptable water-soluble protective colloids include film-forming hydrocolloids such as gelatin, gum arabic, pectin, agar, tragacanth, alginates and the like. The hydrocolloids also include guar sperm meal, e.g. Meyprogat 60(Meyhall Chemical AG), methylcellulose, e.g. Methocel 100 CPS(Dow Chemical) and Tylose C 600(Kalle Chemie, Wiesbaden BRD), sodium carboxymethyl cellulose, modified starches, e.g., Capsul(Roquette National) and Sterimul(H. Kohnstamm & Co. Inc.) and the like.

Examples of emulsifiers include practically all the conventional oil-in-water emulsifiers such as sodium ascorbyl palmitate, a polyoxyalkylene derivative of sorbitan monostearate(Tween 60), mixtures of glycerol mono- and di-ricinoleates with polyoxyethyleneglycol ether groups and monoricinoleic esters of polyethylene glycol(Cremophor, BASF), sugar ester P 1570(Ryoto Co.) and the like.

These edible, water-soluble carrier compositions are usually used in the form of dilute aqueous solutions containing, in percents by weight based on the total weight of the solution, from about 0.1% to about 5% of the water-soluble carrier composition. Solutions containing from about 0.5% to about 2% of the carrier composition are preferred.

The vitamin A acetate used in the process of this invention can be either molten or wet-milled.

The vitamin A acetate is conveniently melted in the aqueous solutions of the carrier compositions by heating the solutions to from about 60° C. to about 70° C.

The crystalline vitamin A acetate is conveniently wet-milled in water alone or in a solution of the carrier composition or in mixtures thereof.

The homogenization technique is a critical factor in the process of this invention since the microcrystalline particles of vitamin A acetate should have a particle size range in the suspension of from about $0.5\mu$ to about $50\mu$ with a particle size range of from about $1\mu$ to about $25\mu$ preferred.

Homogenization can be achieved by several procedures as, for example, pressure homogenization, ultrasonics and, preferably, by the use of rapid flow turbine mixers.

These homogenization techniques use a high shear force to obtain small particle sizes. High shear force relates to the applied forces which cause two contiguous parts of a body to slide relative to each other in a direction parallel to their plane of contact.

In one of the procedures of this invention, the requisite high shear force is achieved by use of a pressure homogenizer. Such pressure homogenizers as, for example, the Gaulin Homogenizer, function by passing a product, under pressure, through a restricted aperture whereupon an instant pressure drop to less than atmospheric pressure occurs. This causes both a shearing action and cavitation bubbles. The product then strikes an impact ring at velocities up to 57,000 feet per minute, further shattering the particles by both impact and implosion of the cavitation bubbles. The homogenized product is then discharged.

In a Gaulin Homogenizer, the restricted aperture is achieved by use of a pre-loaded adjustable valve which is forced open by the flow movement of the pressurized product.

In the preferred procedure of this invention, a technique involving high-speed mixing (i.e. from about 3,000 to about 12,000 rpm) coupled with a high shear force is used. In this procedure, the effective shear force is dependent on the solids content and the viscosity of the medium being mixed, the speed of mixing and the geometry of the mixer and the mixing vessel. A type of mixer which achieves this dual function of high speed mixing and high shear force is, for example, one employing a single shaft mixer with two separated, serrated circular horizontal shear plates set between two inverted feed cones on a single shaft. Using a mixer of this type as, for example, a Lee Turbon mixer, both high speed mixing and high shear force are rapidly achieved.

What is important is achieving the microcrystalline vitamin A acetate of this invention is the obtention of a shear force high enough to provide the requisite particle size range of the vitamin A acetate in the dispersed phase.

The homogenization is preferably carrier out in a dilute aqueous solution of the water-soluble carrier composition.

Once the homogenization is completed, the emulsion is rapidly cooled to below about 15° C. The homogenization technique is continued during the cooling operation. By this process, microcrystals of vitamin A acetate separate from the emulsion. They can be isolated by centrifugation.

To obtain a more stable product, the melting of the vitamin A acetate, its homogenization in the dilute aqueous solution of the carrier composition and the subsequent formation of the microcrystals of the vitamin A acetate should be carried out with the exclusion of oxygen, i.e., in an inert gas atmosphere as, for example, nitrogen, argon and the like.

The microcrystals of vitamin A acetate can be formed into dry free-flowing beadlets by procedures known in the art. For example, microcrystalline vitamin A acetate is dispersed in a gelatin/sugar solution, heated to 40°–50° C. and, then added, with stirring to an oil, e.g. caster oil, paraffin oil. Stirring is continued until visible droplets result. The mixture is cooled with stirring to about 10° C., and then alcohol or a starch are added to either dehydrate or coat the solidified beadlets. The beadlets are separated by filtration, washed with, e.g., alcohol or petroleum, ether and dried. Drying techniques include use of a fluidized bed or vacuum drying.

The microcrystalline Vitamin A acetate particles are preferably coated with a film-forming hydrocolloid such as gelatin.

Compositions containing up to about 500,000 IU/gram can be prepared. Although these compositions do not contain any antioxidants, they exhibit excellent vitamin A stability. For example, a dry powder prepared according to a procedure described in the following Examples has the following stability data:

|  | IU/gram |
|---|---|
| Vitamin A activity, original | 264,000 |
| Vitamin A activity, 3 months at room temperature | 264,000 |
| Vitamin A activity, 3 months at 45° C. | 258,700 |
| Vitamin A activity, 2 days at 70% R.H. and 45° C. | 245,500 |

The dry free-flowing powders of microcrystalline Vitamin A acetate are suitable for use as additives for, e.g., feedstuffs, multivitamin preparations and, especially, foodstuffs.

The following Examples illustrate the invention:

EXAMPLE 1

A 1% aqueous solution of low viscosity gelatin (30 Bloom) was prepared. 50 grams of crystalline vitamin A acetate (2.8 million IU/g) are added to 500 ml. of this gelatin solution. The resulting mixture is heated on a steam bath, under a nitrogen atmosphere, to about 70° C. to melt the vitamin A acetate.

The mixture is then emulsified under a nitrogen atmosphere using an ULTRA-TURRAX homogenizer (Janke and Kunkel, Staufen) at medium rotation. After emulsification and with continued stirring, the emulsion is cooled to below 10° C. using an ice-water bath.

Homogenization is stopped and the resulting suspension of vitamin A acetate microcrystals maintained at about 5° C. under a nitrogen atmosphere until crystallization is complete. This is determined from observations of an aliquot under a microscope at weak magnification. Crystallization is completed in about 2 hours.

The microcrystals are separated from the suspending medium by centrifugation at high speed. The resulting moist crystal mass can be used for the preparation of dry powders.

EXAMPLE 2

A 30% aqueous solution of gelatin (a 2:1 mixture of 200 Bloom gelatin and 300 Bloom gelatin) is prepared and an amount of crystalline sugar equal to one-third of the weight of the gelatin is dissolved therein with warming.

26.5 grams of microcrystalline vitamin A acetate, prepared by the procedure of Example 1, are added to 250 grams of the gelatin/sugar solution and nitrogen is bubbled through the mixture. The mixture is then stirred vigorously for ten minutes while warming to 40°–50° C.

The resulting crystal suspension is then added, over a one minute period, to 600 ml. of caster oil at 45° C. During the addition, the caster oil was mechanically stirred so that visible, fine droplets resulted. After the addition of the crystal suspension was completed, stirring continued while the mixture is cooled to about 10° C. using an ice-methanol bath. When the viscous droplets began to solidify, 600 ml. of ethanol at 50° C. are added to the mixture and stirring is continued for a short period. The formed beadlets, which were partially dehydrated, are separated from the liquid by filtration and washed with cold ethanol.

The beadlets are initially dried by a fluidized bed procedure using cold air. The beadlets are then dried in a vacuum oven at room temperature with a slight flow of air.

The resulting dried beadlets are separated by sieving from the fine powders (less that 10μm) and from any oversized granules. The beadlets assayed about 264,000 IU/gram.

EXAMPLE 3

A crystal vitamin A acetate suspension, prepared as described in Example 2 above, is added with stirring to 600 ml. of a viscous paraffin oil. The stirring is continued while the mixture is cooled to 10° C.

When the viscous droplets began to solidify, 13 grams of a white maize starch, which had been pre-mixed with a small amount of paraffin oil, are added. 200 ml. of low-boiling petroleum ether at about 5° C. are then added and stirring is continued for 10 minutes more.

The white maize starch deposited on and superficially coated the solidified beadlets which are then easily separated from the liquid medium by vacuum filtration. The particles are washed with cold petroleum ether.

Drying is accomplished by use of cold air in a fluidized bed followed by drying at room temperature in a vacuum oven with a slight flow of air.

The dried beadlets are separated by sieving from the fine powders and coarse granules.

We claim:

1. A process for the preparation of dry, free flowing beadlets containing microcrystalline vitamin A acetate which exhibits excellent vitamin A stability without containing any antioxidants and which comprises
   - (a) homogenizing with sufficient high shear force to obtain particle sizes of from about $0.5\mu$ to about $50\mu$ of molten or wet-milled vitamin A acetate in an aqueous solution containing from about 0.1% to about 5% by weight, based on the weight of the solution, of an edible, water-soluble carrier composition selected from the group consisting of gelatin, gum arabic, pectin, agar, tragacanth, alginates, guar sperm meal, methylcellulose, sodium carboxymethyl cellulose, modified starch, sodium ascorbyl palmitate, a polyoxyalkylene derivative of sorbitan mono- annd monostearate, mixtures of glycerol mono- and di-ricinoleates with polyoxyethylene glycol ether groups and monoricinoleic esters of polyethylene glycol;
   - (b) cooling the resulting emulsion to about 15° C. while continuing the homogenization technique until such particle size ranges are obtained, of completely crystalline vitamin A acetate microcrystals;
   - (c) separating the completely crystallized microcrystalline vitamin A acetate from the liquid medium by centrifugation;
   - (d) adding the microcrystalline vitamin A acetate to a gelatin/sugar solution wherein the ratio of gelatin to sugar is about 3 to 1;
   - (e) heating the resulting mixture to from about 40° to about 50° C. with vigorous stirring to suspend the microcrystals;
   - (f) adding the resulting microcrystal suspension of step (e) to an oil which has been heated to 45° C. using sufficient stirring to form fine droplets;
   - (g) cooling the resultant mixture with stirring to from about 5° to about 15° C. to solidify the droplets;
   - (h) washing the beadlets with a solvent for the oil;
   - (i) separating the beadlets from the suspension medium, and
   - (j) drying the beadlets to thus form dry, free-flowing beadlets containing vitamin A acetate in microcrystalline form and which exhibit excellent vitamin A stability without containing any antioxidants.

2. A dry free-flowing vitamin A powder composition which exhibits excellent vitamin A stability without containing any antioxidants and which comprises microcrystalline vitamin A acetate coated with an edible, water-soluble carrier composition produced by the process of claim 1.

3. A process for the preparation of microcrystalline vitamin A acetate which comprises
   - (a) homogenizing with sufficient high shear force to obtain particle sizes of from about $0.5\mu$ to about $0.5\mu$ of molten or wet-milled vitamin A acetate in water or an aqueous solution containing from about 0.1% to about 5% by weight, based on the weight of the solution, of an edible, water-soluble carrier composition selected from the group consisting of gelatin, gum arabic, pectin, agar, tragacanth, alginates, guar sperm meal, methylcellulose, sodium carboxymethyl cellulose, modified starch, sodium ascorbyl palmitate, a polyoxyalkylene derivative of sorbitan monosterate, mixtures of glycerol mono- and di-ricinoleates with polyoxyethylene glycol ether groups and monoricinoleic esters of polyethylene glycol, and
   - (b) cooling the resulting emulsion to about 15° C. while continuing the homonegization technique to thus obtain microcrystals of vitamin A acetate.

4. The process of claim 3 wherein the edible water-soluble carrier material is gelatin.

5. The process of claim 3 wherein the vitamin A acetate, after homogenization, has a particle size range of from about $0.5\mu$ to about $50\mu$.

6. The process of claim 3 wherein the vitamin A acetate, after homogenization, has a particle size range of from about $1\mu$ to about $25\mu$.

7. The dry, free-flowing vitamin A powder composition of claim 2 wherein the edible water-soluble carrier composition is gelatin.

8. The process of claim 1 wherein the edible, water-soluble carrier composition is gelatin.

9. The process of claim 1 wherein the vitamin A acetate, after homogenization, has a particle size range of from about $0.5\mu$ to about $50\mu$.

10. The process of claim 9 wherein the vitamin A acetate, after homogenization, has a particle size range of from about $1\mu$ to about $25\mu$.

11. Dry, free-flowing vitamin A beadlets which comprise the vitamin A powder composition of claim 2 within a gelatin/sugar coating.

* * * * *